United States Patent
Kobren

[11] Patent Number: 5,953,751
[45] Date of Patent: Sep. 21, 1999

[54] NEEDLESTICK RESISTANT MEDICAL GLOVE

[76] Inventor: Myles S. Kobren, 100 Manetto Hill Rd. - Suite 302, Plainview, N.Y. 11803

[21] Appl. No.: 08/977,169

[22] Filed: Nov. 24, 1997

[51] Int. Cl.$^6$ ..................................................... A41D 13/08
[52] U.S. Cl. ..................................................... 2/16; 2/161.7
[58] Field of Search ................. 2/16, 21, 159, 2/160, 161.1, 161.6, 161.7, 163

[56] References Cited

U.S. PATENT DOCUMENTS

| | | | |
|---|---|---|---|
| 3,732,575 | 5/1973 | Pakulak | 2/161.6 |
| 4,272,849 | 6/1981 | Thurston et al. | 2/161.6 |
| 4,694,508 | 9/1987 | Iriyama et al. | 2/161.6 |
| 4,864,661 | 9/1989 | Gimbel | 2/161.6 |
| 4,951,689 | 8/1990 | Jones | 2/160 |
| 5,113,526 | 5/1992 | Wang et al. | 2/161.6 |
| 5,368,930 | 11/1994 | Samples | 2/161.6 |

FOREIGN PATENT DOCUMENTS

| | | | |
|---|---|---|---|
| 97224 | 1/1924 | Australia | 2/161.1 |
| 2290857 | 6/1976 | France | 2/161.6 |

*Primary Examiner*—John J. Calvert
*Assistant Examiner*—Larry D. Worrell, Jr.
*Attorney, Agent, or Firm*—Eliot S. Gerber

[57] ABSTRACT

A needlestick resistant glove for surgical and other medical uses includes a flexible and elastic web which fits the user's hand. In one embodiment the web is partly covered by custom-fitted curved plates. The flexible web areas between the plates comprise hemispherical or disk protrusions. In another embodiment, without plates, the protrusions on the web are disks and the areas between the disks are covered by other disks.

2 Claims, 3 Drawing Sheets

NEEDLESTICK RESISTANT MEDICAL GLOVE

FIELD OF THE INVENTION

The present invention relates to medical devices and more particularly to a needlestick resistant medical glove.

BACKGROUND OF THE INVENTION

At the present time there is an increased concern about the spread of infectious diseases to health care workers due to accidental skin punctures. Various diseases, especially HIV (AIDS) and hepatitis may be transmitted when the patient's blood is on a medical instrument which cuts the skin of a physician or nurse. That may occur from a needle ("needlestick") during an injection or test or from a surgical instrument during an operation. If a transfer of diseased blood occurs, regardless of the quantity, it may cause infection, illness and death.

The patent literature has many patents which attempt to solve this problem using special gloves. Many of the patented suggestions appear to provide gloves which are too bulky or heavy for practical use. In any event, there apparently are no such gloves in wide use in the medical field, although there is a need for such protective gloves.

U.S. Pat. No. 4,742,578 entitled "Penetration-Resistant Surgical Glove" discloses a large number of tightly interlaced fibers adhered to a latex (thin rubber) glove. U.S. Pat. No. 4,779,290 entitled "Cut-Resistant Surgical Gloves" relates to a hand mold dipped into a curable liquid, lined with flexible armor, and dipped again into the curable liquid. U.S. Pat. No. 5,187,385 uses two flexible layers and an optional layer of corrugated metal foil. U.S. Pat. No. 5,368,930 entitled "Thin Elastomeric Article Having increasing Puncture Resistance" discloses thin plate-like non-elastic particles in an elastomeric matrix. U.S. Pat. No. 5,564,127 entitled "Puncture-Proof Surgical Glove" employs knitted material of high tensile strength fibers. Other patents for protective medical gloves are U.S. Pat. Nos. 4,951,689; 4,901,372; 4,942,626 and 5,070,540.

SUMMARY Of THE INVENTION

The present invention presents a protective glove, especially for surgery as well as general medical use. The glove is flexible so the user may perform his/her usual functions. The glove is sufficiently closely fitting so the user retains much of the feeling response from the hand. The glove is light in weight and permits vapor removal so that the user's hands do not over-heat and become sweaty. These features are not present in the gloves of the prior art discussed above.

The first embodiment uses a series of lightweight rigid plates for each glove. For example, each finger will have as many as eight, or as few as three, thin and curved plates. Preferably the plates are of a puncture resistant and lightweight material, preferably titanium or carbon fiber reinforced plastic. The plates are selected, or molded, to conform to the size and shape of each user, i.e., the plates, and gloves are custom-fitted to the individual.

The second embodiment uses a layer of tiny and rigid plates on a flexible support web. The web material and glove are flexible, because of the flexible support, and the glove resists needlesticks, because of the plates. Preferably the plates and support are formed as one member from a reinforced plastic by precision molding, i.e., the plates are protrusions on a plastic sheet. The spaces between the plates are preferably covered by another layer of plates which are fixed to the support web in a flexible manner.

DETAILED DESCRIPTION OF THE INVENTION

Figure 1:
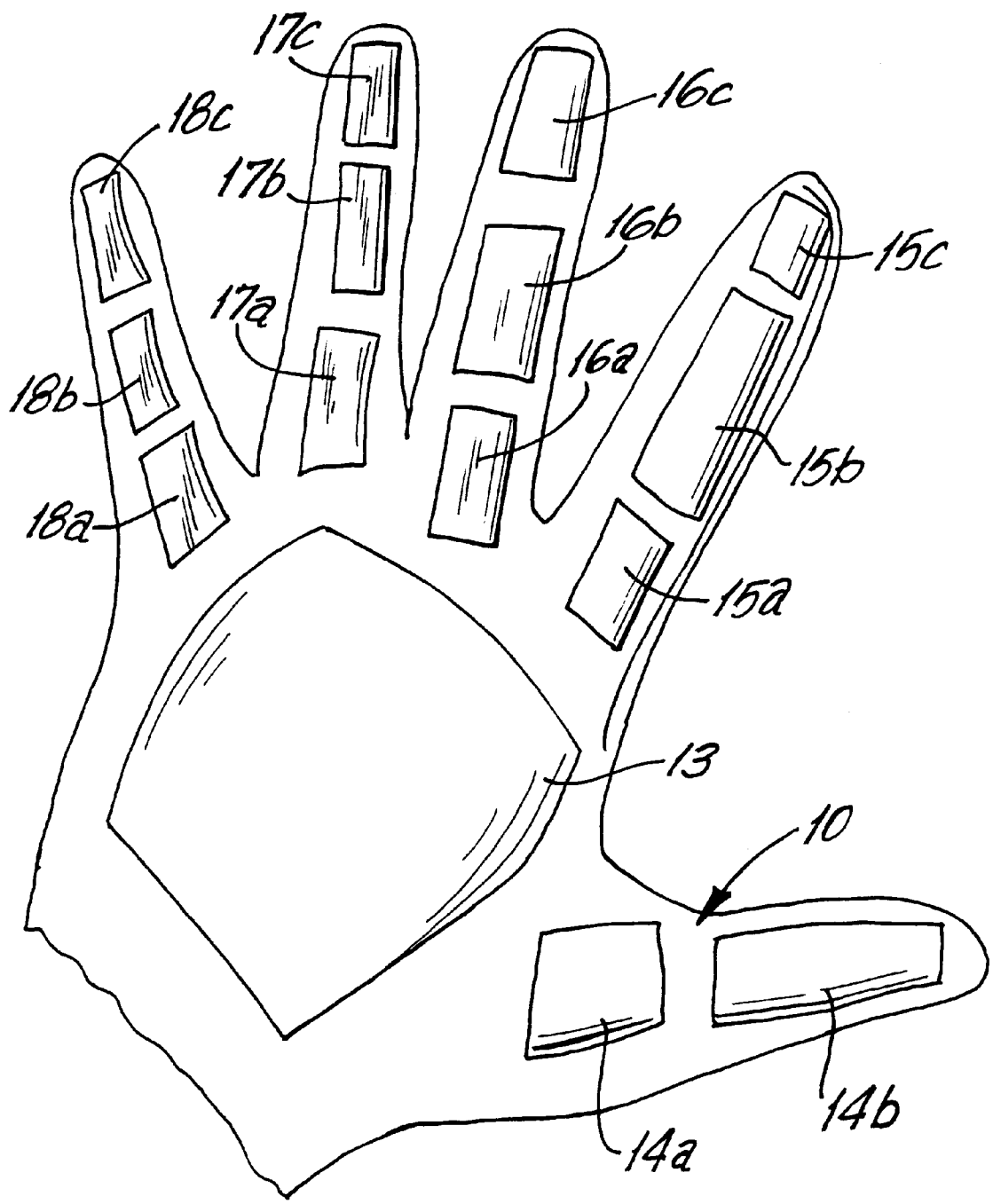
FIG. 1 is a top plan view of a right-hand glove of the first embodiment using custom-fit plates.

As shown in FIG. 1, the protective glove 10 is a simple, lightweight and inexpensive device. It consists of a high-grade elastic web 11 formed as a glove. The web material should be sterilizable so that the glove may be sterilized and reused. Alternatively, the web material may be a thinner material, such as latex, and the glove 10 be considered disposable.

The glove has a series of curved plates 12 consisting of a large plate 13, for the back of the hand, and smaller plates for the fingers. Each of the fingers (except for the thumb) has three plates. The thumb has plates 14a,14b, the first finger has plates 15a–15c, the middle finger has plates 16a–16c, the next (ring) finger has plates 17a–17c, and the little finger has plates 18a–18c.

The plates 12 are made of a strong and lightweight material. They are sufficiently thick to resist an accidental needle jab. A preferred material is a titanium or aluminum or reinforced plastic sheet of 0.01 mm to 0.2 mm. A suitable plastic is a carbon filament reinforced epoxy resin.

An inexpensive throw-away glove may be manufactured by forming the curvatures to fit a limited number of hands, i.e., sized as glove, i.e., 8, 8½, 9, etc.

A preferred method is to take a mold of the user's hands and then produce gloves which are custom fitted to the individual. For example, the plate curvature 15a may be selected, by the glove manufacturer, from 10–20 standard curvatures, the selection being based on the user's hand mold.

Figure 2A:
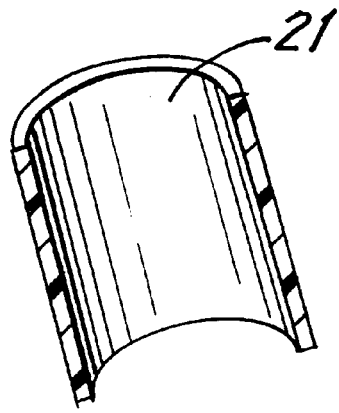
FIGS. 2A and 2B are enlarged views of custom-fit plates.
Figure 2B:
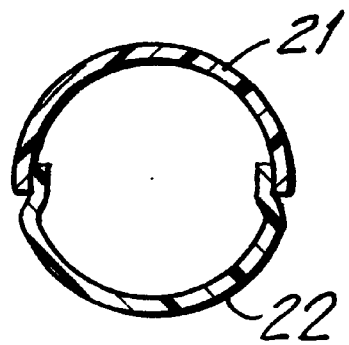

In the glove using the plates of FIGS. 2A and 2B the plates 12 are provided on top and bottom and the sides of each finger. In this embodiment, showing the curved plates 21 and 22 of one finger, the plates overlap so that the amount of unprotected skin is minimized.

Plate 21 (FIG. 2A) is one-half of a tube and overlaps with a plate 22 (see FIG. 2B). Alternatively, plates 21A and 21B may be formed as a tube.

Figure 3:
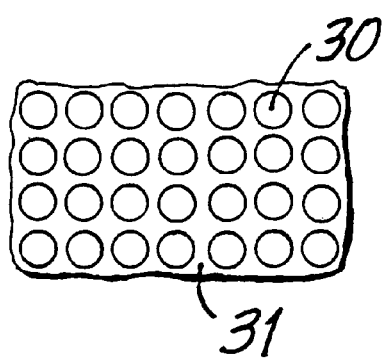
FIG. 3 is a top plan view, enlarged, of a portion of the fabric of the second embodiment using tiny round plates on a flexible support web.
Figure 4:
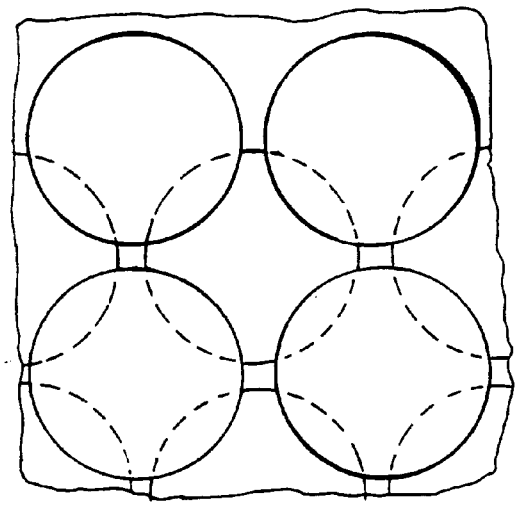
FIG. 4 is an enlarged top view of the plate of FIG. 3 overlapped with cover plates.

The embodiment of FIGS. 3–6 is a different structure in which the material of the glove is flexible and yet resists needlesticks. As shown in FIG. 3 a series of tiny disks 30 are formed side-by-side on a flexible web 31. Preferably, as shown in FIG. 4, the web and disks (protrusions) are formed as an integral plastic molded sheet. The web 31 is the thin portion between the disks and is flexible because it is thin. For example, the disks are 0.1 mm to 0.2 mm thick and the web 31 (between the disks) is from 0.01 mm to 0.2 mm thick. The plastic is preferably a carbon fiber impregnated plastic resin and the gloves are molded in suitable sizes, i.e., 8, 8½, 9, etc.

Figure 5:
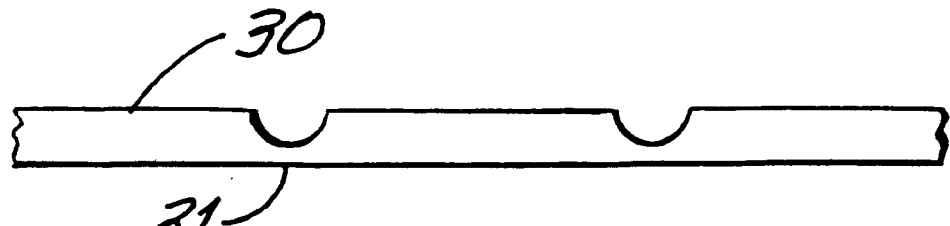
FIG. 5 is an enlarged side cross-sectional view of the layer of FIG. 3.
Figure 6:
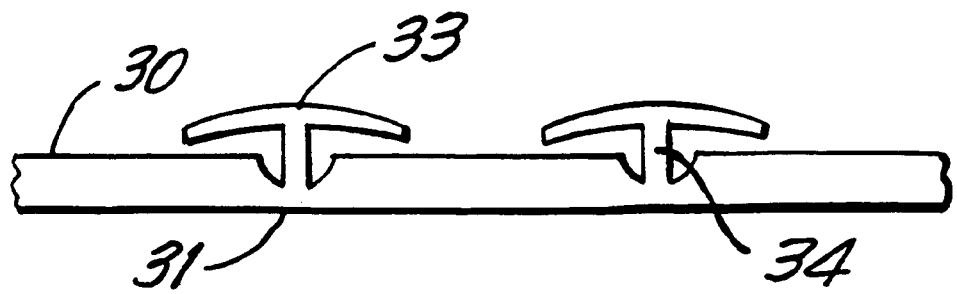
FIG. 6 is an enlarged side cross-sectional view of the overlapped plates of FIG. 4.

As shown in FIGS. 4 and 6, a second layer of disks may be used to overlap the first layer (FIGS. 3 and 5). The second layer consists of disks 33 which have integral stems 34. The stems 34 are integral with, or attached to, the web 31. An elastic (latex) glove may be worn over the plates to provide a smooth outer surface.

Figure 7:
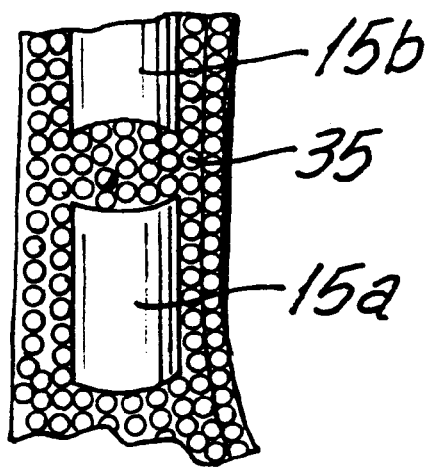
FIG. 7 is an enlarged top view of one figure of a glove.

The embodiment of FIG. 7 uses the curved plates of FIG. 1 and a needlestick resistant flexible web 35 between the plates. Preferably the web 35 consists of small hemispheres which are integral with a support layer. Preferably the web 35 is formed from a strong injection molded plastic. Alternatively, the web 35 may consist of two, or more, layers each of which has small disks or hemisphere-shaped protrusions on a flexible support layer.

What is claimed is:

1. A needlestick resistant plastic hand glove for medical personnel comprising an injection-molded flexible plastic glove; the sheet comprising a flexible one-piece web and integral therewith a set of plastic protruding disks positioned side-by-side with spaces therebetween;

the disks being without a hole, having a diameter less than 1 cm and being in the range of 0.01 to 1 mm thick.

2. A needlestick resistant plastic hand glove for medical personnel comprising an injection-molded flexible plastic glove; comprising a flexible one-piece web and integral therewith a first set of plastic protruding disks positioned side-by-side with spaces therebetween;

the disks being without a hole, having a diameter less than 1 cm and being in the range of 0.01 to 1 mm thick; and a second set of side-by-side disks overlapping the disks of the first set and flexibly fixed to the web.

* * * * *